US011771342B2

(12) United States Patent
Malcolm

(10) Patent No.: US 11,771,342 B2
(45) Date of Patent: Oct. 3, 2023

(54) MAGNETIC HEIGHT-MEASURING DEVICE

(71) Applicant: Dwayne A. Malcolm, Floral Park, NY (US)

(72) Inventor: Dwayne A. Malcolm, Floral Park, NY (US)

( * ) Notice: Subject to any disclaimer, the term of this patent is extended or adjusted under 35 U.S.C. 154(b) by 267 days.

(21) Appl. No.: 17/170,092

(22) Filed: Feb. 8, 2021

(65) Prior Publication Data

US 2021/0244315 A1 Aug. 12, 2021

Related U.S. Application Data

(60) Provisional application No. 62/970,859, filed on Feb. 6, 2020.

(51) Int. Cl.
*A61B 5/107* (2006.01)
*G01C 5/00* (2006.01)

(52) U.S. Cl.
CPC .............. *A61B 5/1072* (2013.01); *G01C 5/00* (2013.01)

(58) Field of Classification Search
CPC .................................................. A61B 5/1072
(Continued)

(56) References Cited

U.S. PATENT DOCUMENTS 2,324,334 A * 7/1943 Sutton ................. A61B 5/1072
33/512
4,134,212 A * 1/1979 Allen ..................... G01B 3/004
33/512

(Continued)

*Primary Examiner* — George B Bennett
(74) *Attorney, Agent, or Firm* — Alan M. Sack; SACK IP Law p.c.

(57) ABSTRACT

A device for measuring the height of an individual subject, which includes an elongated body member having a front surface which visually displays units of measure, i.e., inches, each measuring unit being divided into fractions of the measuring unit which are depicted on the front surface. The body member is attachable to a vertical wall surface above a generally horizontal floor surface by any known means, such as by attaching a pair of steel bars to the wall surface, and attaching, or preferably embedding, a plurality of rare earth magnets to the body member, i.e., about two magnets for each steel bar.

A height indicating guide member is releasably and slidably attached to the body member by a metal strip being embedded and hidden from view into a side of the body member, and several rare earth magnets, preferably four, being attached, or preferably embedded into a side surface of the guide member. The slidable guide member has an outwardly extending height indicating member attached thereto. The outwardly extending height indicating member has a height measuring bottom surface which is generally horizontal and parallel to the floor surface, such that the distance between the horizontal surface and the floor surface is visually indicated on the body member. The body member is attached to a wall surface at a vertical position which depicts the distance between the measurement units and the floor.

When the individual subject is positioned adjacent the body member and the guide member is slid to a position where the lower horizontal height measuring surface contacts the uppermost surface of the head of the individual subject, the height of the individual subject will be indicated on the body member. A height information chart board is conveniently slidably inserted into a slot of the body member, the chart board having a writing surface for recording the height of an individual subject, I.e., a child as he or she is growing up. The chart board is releasably attached to the body member by a plurality of magnets, preferably rare earth magnets. The body member is preferably comprised of two sections attached by hinges so that it can be folded for storage or transport.

5 Claims, 5 Drawing Sheets

(58) Field of Classification Search
USPC .......................................................... 33/512
See application file for complete search history.

(56) References Cited

U.S. PATENT DOCUMENTS

| | | | | |
|---|---|---|---|---|
| 6,073,359 | A * | 6/2000 | Lee | A61B 5/1072 33/DIG. 1 |
| 6,226,881 | B1 * | 5/2001 | Landauer | G01B 5/061 33/511 |
| 7,891,106 | B2 * | 2/2011 | Dunham | A61B 5/1072 33/486 |
| 8,539,690 | B2 * | 9/2013 | Haykeen | A61B 5/1072 600/587 |
| 8,845,332 | B1 * | 9/2014 | Reid | A61B 5/1072 702/173 |
| 8,869,415 | B1 * | 10/2014 | Haykeen | A61B 5/1072 33/485 |
| 10,788,305 | B1 * | 9/2020 | Neu | G01B 3/1048 |
| 11,172,847 | B2 * | 11/2021 | Johnston | G01B 11/0608 |
| 11,382,532 | B1 * | 7/2022 | Hajianpour | G01B 5/061 |
| 2011/0072677 | A1 * | 3/2011 | Hong | A61B 5/1072 33/832 |
| 2012/0096726 | A1 * | 4/2012 | Glock, Jr. | A61B 5/1072 33/512 |
| 2012/0144686 | A1 * | 6/2012 | Haykeen | A61B 5/1072 33/512 |
| 2014/0109425 | A1 * | 4/2014 | Brotman | G01B 3/10 33/759 |
| 2014/0202017 | A1 * | 7/2014 | Wood | G01B 3/20 33/512 |
| 2015/0135544 | A1 * | 5/2015 | Jesse | A61B 5/1072 33/493 |

* cited by examiner

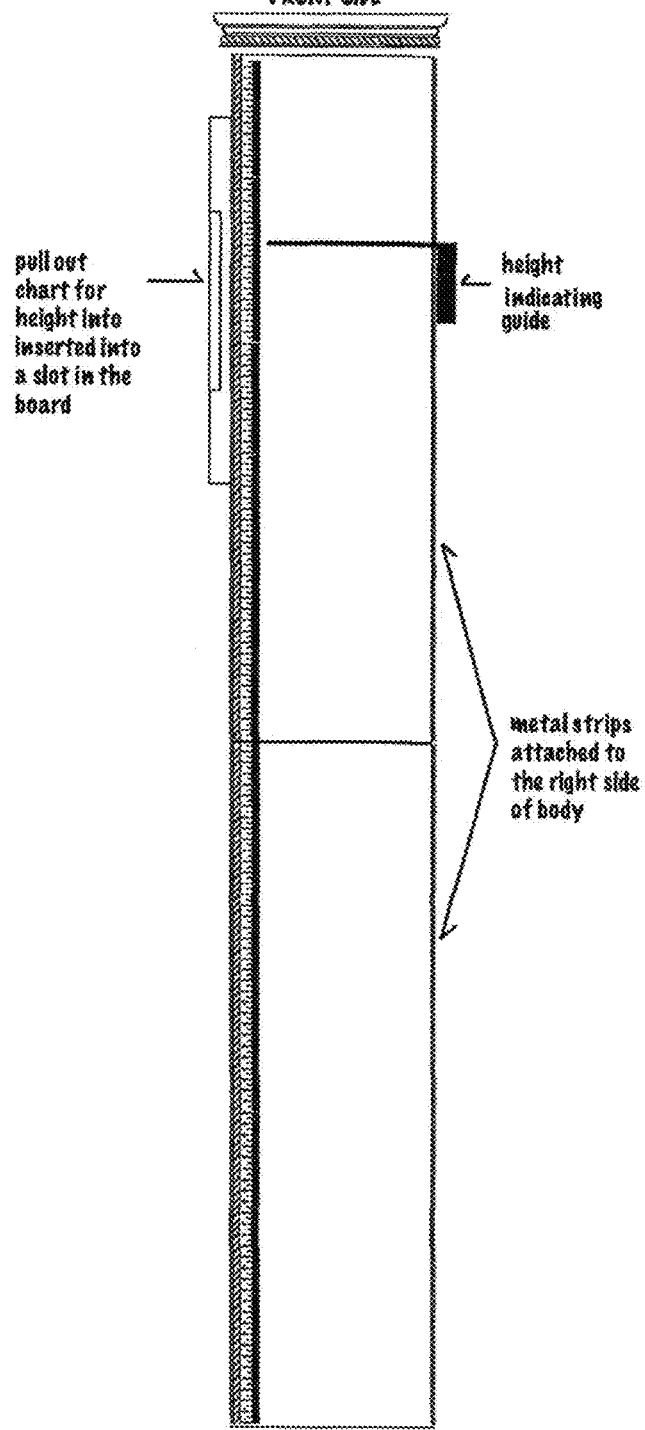
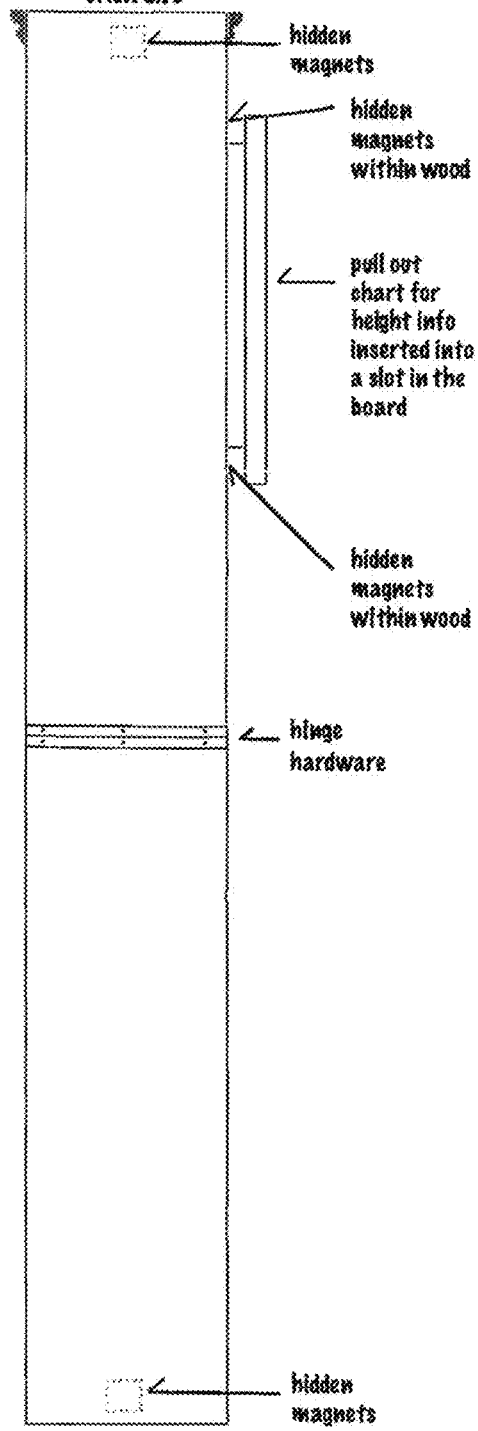

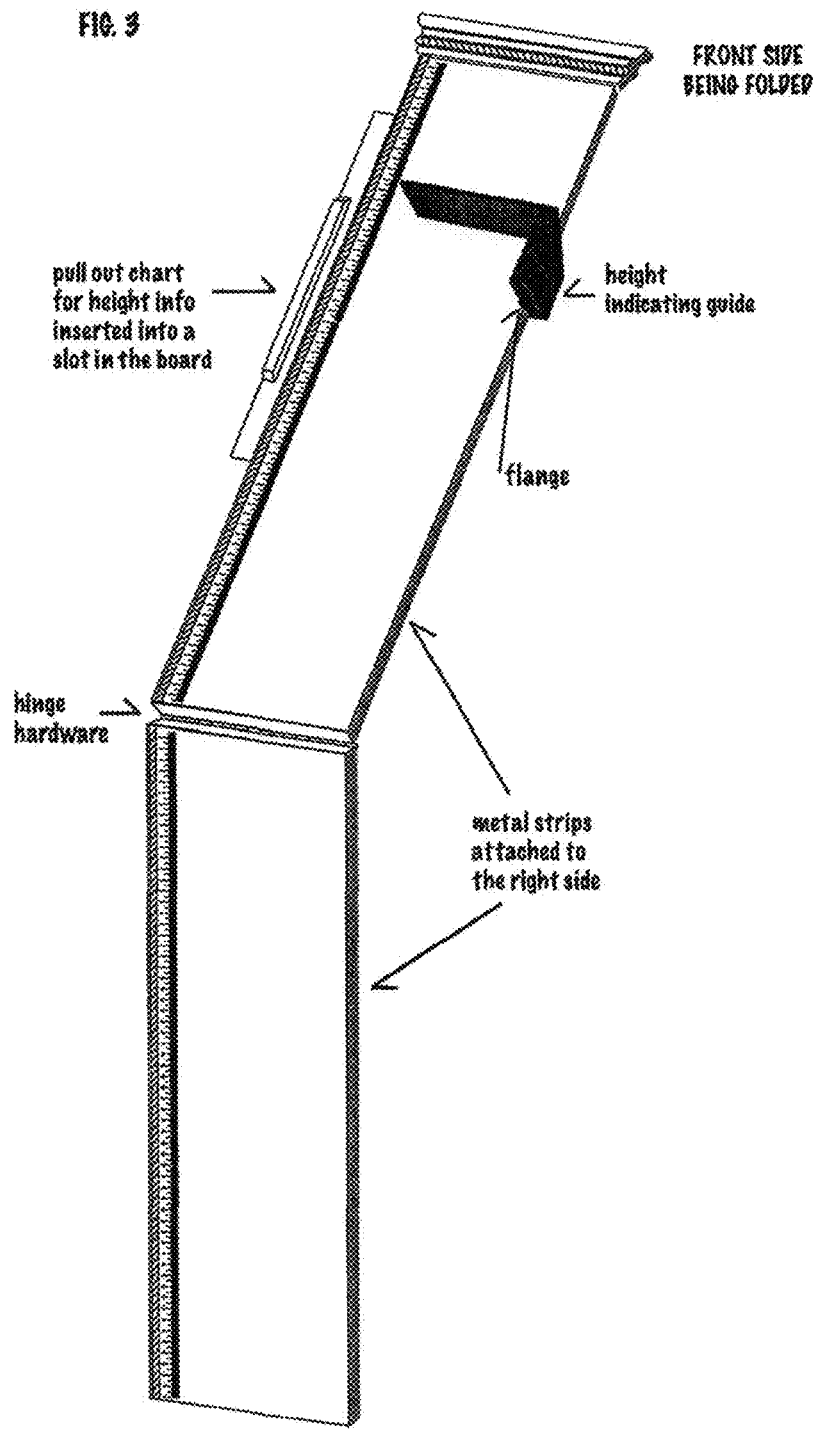

Magnetic Height Measuring Device
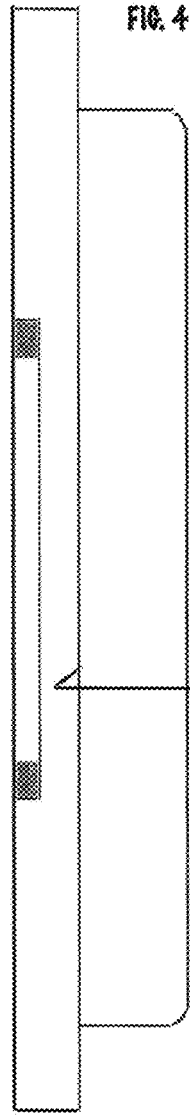
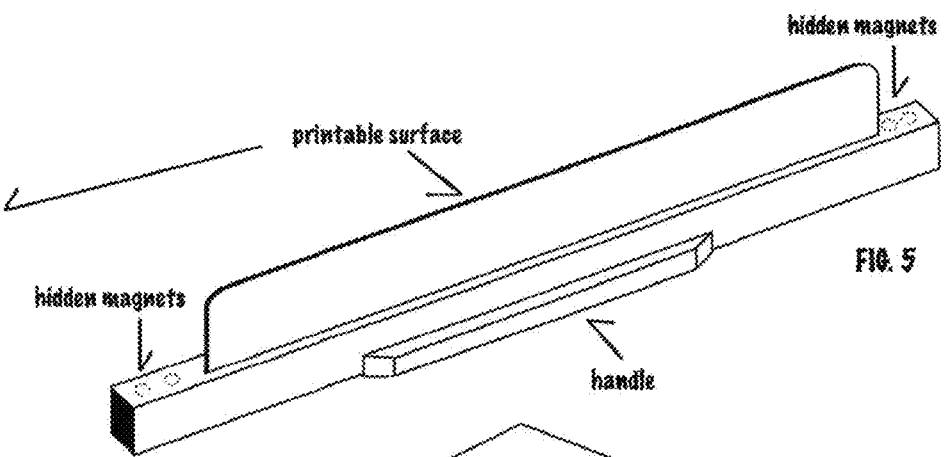
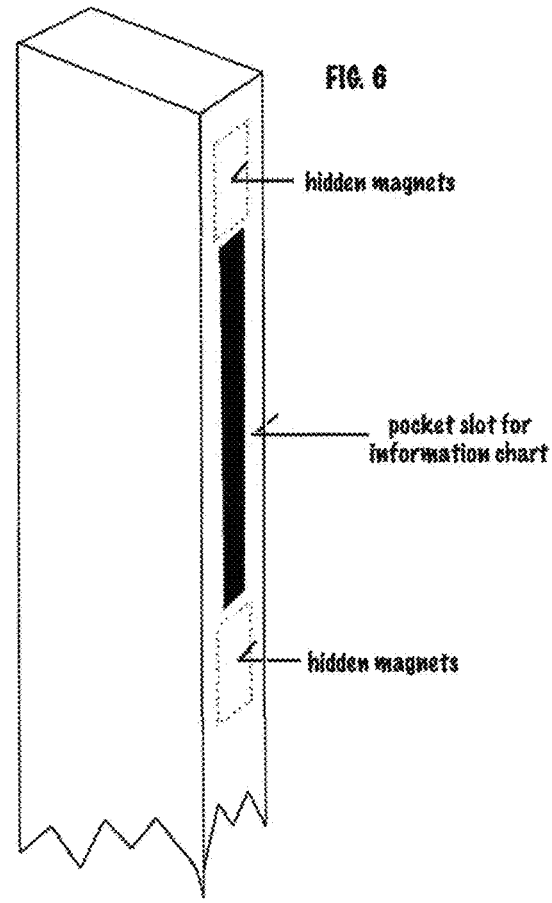

Magnetic Height Measuring Device magnets embedded in wood and finished to hide section on adjustable guide sits on the head of person being measured horizontal measuring surface wall hanging hardware with magnets magnet side view

MAGNETIC HEIGHT-MEASURING DEVICE

CROSS REFERENCE TO RELATED APPLICATIONS

This application claims priority to Application No. 62/970,859, filed Feb. 6, 2020, the contents of which are incorporated by reference and made a part of this application.

DISCLOSURE OF THE INVENTION

A magnetic height-measuring device is designed to provide the user with a convenient and innovative way to measure the height of children and adults alike with the ability for the magnetic height-measuring device to be folded into a smaller configuration, e.g., in half, as a result of the installed piano hinges. The magnetic height-measuring device contains multiple magnets, e.g., neodymium rare earth magnets. The magnets facilitate movable contact between multiple moving parts on the height-measuring device, including:

Up and down movement of the height adjusting slider; and

In and out movement of the height information chart board

Additionally, magnets are used for supporting the device on a wall with the need to disassemble the device for transport.

Internal magnets within the magnetic height-measuring device provide additional benefits whether the user wishes to hang the device on the wall, fold it away after each time it is used or fold for ease of transport. The magnets can be used to:

Affix the magnetic height-measuring device to a wall with the use of magnetized wall hanging hardware.

Hold the magnetic height-measuring device in-place when folded in half for storage or transport.

In one embodiment, the magnetic height-measuring device is made of wood, magnets, at least one hinge and a metal strip. The illustrated embodiment comprises a foldable body having a front surface. For example, the body of the device can be formed of wood or a wood-like composite material having overall dimensions of six feet in length, 5½ inches wide and ¾ of an inch in thickness. Piano or other type hinges provide the ability to fold the magnetic height-measuring device so that the body is only about three feet in length for ease of storage or transport.

More hinges will allow a smaller configuration.

A measuring "tape" or similar height markings are positioned on the front surface of the body. A first side surface of the body is covered with a magnetic metal strip. As used herein, the term "magnetic metal" is used to indicate that the material is normally attracted to a magnet.

A slidable height indicating guide is movably connected to the first side of the body. In the illustrated embodiment, the height indicating guide is formed of the same material as the body. The slidable height indicating guide has a horizontal measuring surface which is used to indicate a person's height on the measuring tape and a magnetic side surface designed to movably adhere to the body while sliding along a side surface of the body. The slidable height indicating guide also has a flange comprising a rear surface designed to slide along the front surface of the body proximate the first side for maintaining the front-to-rear position of the height indicating guide. One or more magnets are embedded in the height indicating guide under the magnetic side surface to provide the magnetic properties to the height indicating guide.

These magnets are preferably encased within the body of height indicating guide and not normally visible. The magnets can be embedded by forming slots in the side surface, inserting the magnets and then filling the slots with wood putty or a similar non-magnetic filler. In this manner, the height indicating guide can easily be moved vertically along the first edge of the body to selectively position the height indicating guide on the top of a person's head or to some other desired position. When the horizontal measuring surface is aligned with the top of a person's head, the person's height can be readily read on the measuring tape or other height indicia.

Depending on the positioning of the measurement markings, the magnetic height-measuring device should be installed so that the bottom of the magnetic height-measuring device is exactly the same height above the floor as the starting measurement on the measuring tape.

For example, if the measuring tape starts at 12 inches, then the measuring device should be hung exactly 12 inches above the floor. In one embodiment, the measuring tape affixed to the magnetic height-measuring device begins at 12 inches and ends at 81½ inches.

In the illustrated embodiment, crown molding is attached to the top of the magnetic height-measuring device, along with a decorative molding on the left side (as you face the device) to give the device more of a decorative appearance.

The illustrated embodiment also comprises a pullout chart board comprising a writing surface on which information, such as names, dates and heights can be recorded and stored for a future reference view of the magnetic height-measuring device.

A height-measuring device is designed to provide the user with a convenient and innovative way to measure the height of children and adults alike with the ability for the magnetic height-measuring device to be folded into a smaller configuration, e.g. in half, as a result of the installed piano hinges. The magnetic height-measuring device contains multiple magnets, e.g., neodymium, or other rare earth magnets. The magnets facilitate movable contact between multiple moving parts on the height-measuring device, including:

Up and down movement of the height adjusting slider; and

In and out movement of the height information chart board

Additionally, magnets are used for supporting the device on a wall with the capability to disassemble the device for transport.

A pair of rectangular shaped steel bars are attached to a wall by screws, and a body member of the height measuring device has two pairs of neodmium magnets embedded into the back side for releasably attaching the body member to the wall.

Internal magnets within the magnetic height-measuring device provide additional benefits, whether the user wishes to hang the device on the wall, fold it away after each time it is used, or fold for ease of transport. The magnets can be used to:

Affix the magnetic height-measuring device to a wall with the use of magnetized wall hanging hardware, such as neodmyium magnets and the aforementioned pair of steel bars that are screwed to the wall; or Hold the magnetic height-measuring device in-place when folded in half for storage or transport.

SUMMARY OF THE INVENTION

A device for measuring the height of an individual subject is disclosed, which includes an elongated body member having a front surface which visually displays units of measure, i.e., inches, centimeters or the like, each measuring unit being divided into fractions of the measuring unit which are depicted on the front surface.

The body member is attachable to a vertical wall surface above a generally horizontal floor surface by any known means, such as by attaching a pair of steel bars to the wall surface, and attaching, or preferably embedding, a plurality of rare earth magnets to the body member, i.e., about two magnets for each steel bar.

A height indicating guide member is releasably and slidably attached to the body member by a metal strip being embedded and hidden from view into a side of the body member, and several rare earth magnets, preferably four, being attached, or preferably embedded into a side surface of the guide member.

The slidable guide member has an outwardly extending height indicating member attached thereto. The outwardly extending height indicating member has a height measuring bottom surface which is generally horizontal and parallel to the floor surface, such that the distance between the horizontal surface and the floor surface is visually indicated on the body member. The body member is attached to a wall surface by any known hardware, at a vertical location which depicts the distance between the measurement units and the floor.

When the individual subject is positioned adjacent the body member and the guide member is slid to a position where the lower horizontal height measuring surface contacts the uppermost surface of the head of the individual subject, the height of the individual subject will be indicated on the body member. A height information chart board is conveniently slidably inserted into a slot of the body member, the chart board having a writing surface for recording the height of an individual subject, i.e., a child as he or she is growing up. The chart board is releasably attached to the body member by a plurality of magnets, preferably rare earth magnets. The body member is preferably comprised of two sections attached by hinges so that it can be folded for storage or transport.

In one embodiment, the magnetic height-measuring device is made of wood, magnets, at least one hinge and a metal strip. The illustrated embodiment comprises a foldable body having a front surface. For example, the body of the device can be formed of wood or a wood-like composite material having overall dimensions of at least six feet in length, 5½ inches wide and ¾ of an inch in thickness. Piano or other type hinges provide the ability to fold the magnetic height-measuring device so that the body is only about three feet in length for ease of storage or transport. More hinges will allow a smaller configuration.

A measuring "tape" or similar height markings are positioned on the front surface of the body. A first side surface of the body is covered with a magnetic metal strip.

As used herein, the term "magnetic metal" is meant to indicate that the material is normally attracted to a magnet.

A slidable height indicating guide is movably connected to the first side of the body. In the illustrated embodiment, the height indicating guide is formed of the same material as the body. The slidable height indicating guide has an extension having a horizontal measuring surface which is used to indicate a person's height on the measuring tape, and a magnetic side surface designed to movably adhere to the body while sliding along a side surface of the body. The slidable height indicating guide also has a flange comprising a rear surface designed to slide along the front surface of the body proximate the first side for maintaining the front-to rear position of the height indicating guide. One or more magnets are embedded in the height indicating guide under the magnetic side surface to provide the magnetic properties to the height indicating guide.

These magnets are preferably encased within the body of height indicating guide and not normally visible. The magnets can be embedded by forming slots in the side surface, inserting the magnets and then filling the slots with wood putty or a similar non-magnetic filler. In this manner, the height indicating guide can easily be moved vertically along the first edge of the body to selectively position the height indicating guide on the top of a person's head or to some other desired position. When the horizontal measuring surface is aligned with the top of a person's head, the person's height can be readily read on the measuring tape or other height indicia.

Depending on the positioning of the measurement markings, the magnetic height-measuring device should be installed so that the bottom of the magnetic height-measuring device is exactly the same height above the floor as the starting measurement on the measuring tape.

For example, if the measuring tape starts at 12 inches, then the measuring device should be hung exactly 12 inches above the floor. In one embodiment, the measuring tape affixed to the magnetic height-measuring device begins at 12 inches and ends at 81½ inches.

In the illustrated embodiment, crown molding is attached to the top of the magnetic height-measuring device, along with a decorative molding on the left side (as you face the device) to give the device more of a decorative appearance. The illustrated embodiment also comprises a pullout chart board comprising a writing surface on which information, such as names, dates and heights can be recorded and stored for future reference.

BRIEF DESCRIPTIONS OF THE DRAWINGS

Preferred embodiments of the invention are disclosed herein wherein:

FIG. 1 depicts a front facing according to the invention;

FIG. 2 depicts a rear facing view of the magnetic height-measuring device of FIG. 1;

FIG. 3 depicts a front perspective view of the magnetic height-measuring device in the folded configuration;

FIGS. 4 and 5 depict front and side, perspective views, respectively, of the height information chart board;

FIG. 6 is a partial view of the left side of the body;

Figure 8:
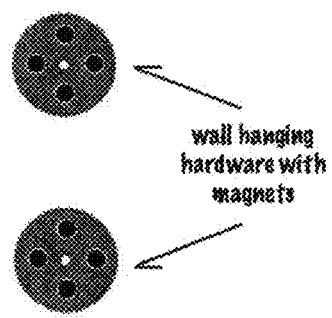
Figure 9:
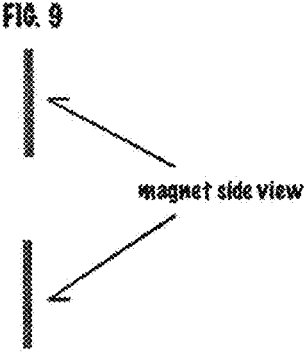
Figure 10:
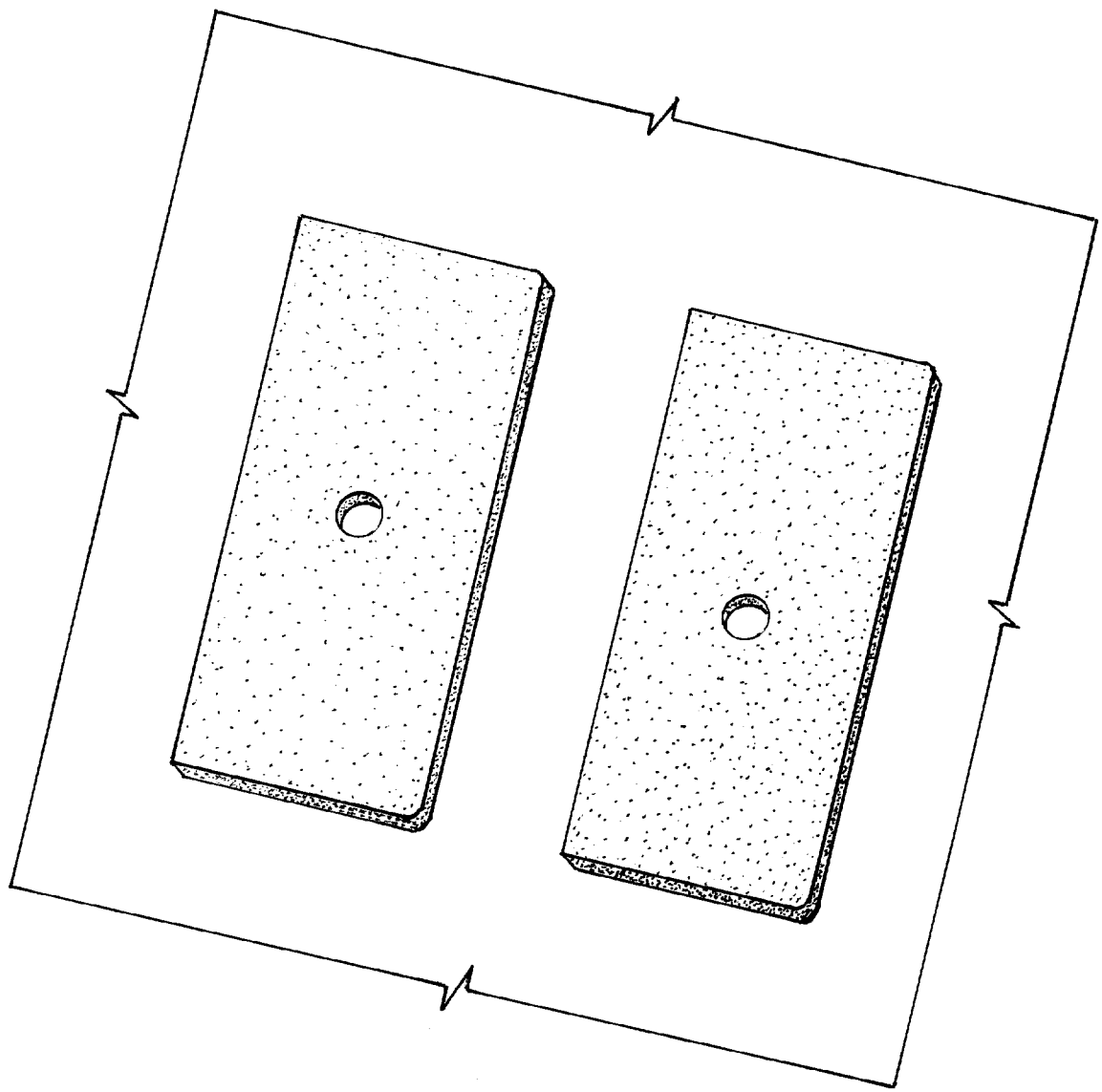

FIGS. 8 and 9 are front and side views, respectively, of the magnetic wall hanging hardware; and FIG. 10 is a depiction of a pair of steel bars that are attached to the wall by screws so that the corresponding magnets embedded into the rear surface of the body member can be used to releasably attach the body member to the wall at a selected height such that the measuring indicia on the front face of the body member indicate their distance to the floor.

DETAILED DESCRIPTION OF THE PREFERRED EMBODIMENTS

FIGS. 1-3 Magnetic Height-Measuring Device

FIG. 1 depicts a front facing view of the magnetic height-measuring device with the two moving parts, a vertically slidable height indicating guide and a horizontally slidable height information chart board. FIG. 1 also illustrates the positioning of the metal strip which supports the height indicating guide via the magnets embedded in the left facing side of the height indicating guide.

FIG. 2 depicts a rear facing view of the magnetic height-measuring device with the height information chart board partially pulled out from the body. Four separate areas are identified where the hidden magnets are located within the body. Two of the hidden magnets are located within the wood proximate the slot for the height information chart board. Two additional hidden magnets, for hanging installation, are located within the body proximate the top and bottom of the body. The hinge hardware, that allows the magnetic height-measuring device to be folded in half for storage or transport is positioned approximately midway between the top and bottom of the body.

FIG. 3 depicts a front perspective view of the magnetic height-measuring device being folded in half for storage or transport.

FIGS. 4 and 5 CHART BOARD

Depict front and side, perspective views, respectively, of the height information chart board. These views illustrate where the hidden magnets are located, as well as the handle to move the height information chart board, in and out of the body.

FIG. 6 Partial View of Body

FIG. 6 is a partial view of the left side of the body indicating a position for hidden magnets in the body above and below the slot for the chart board.

Figure 7:
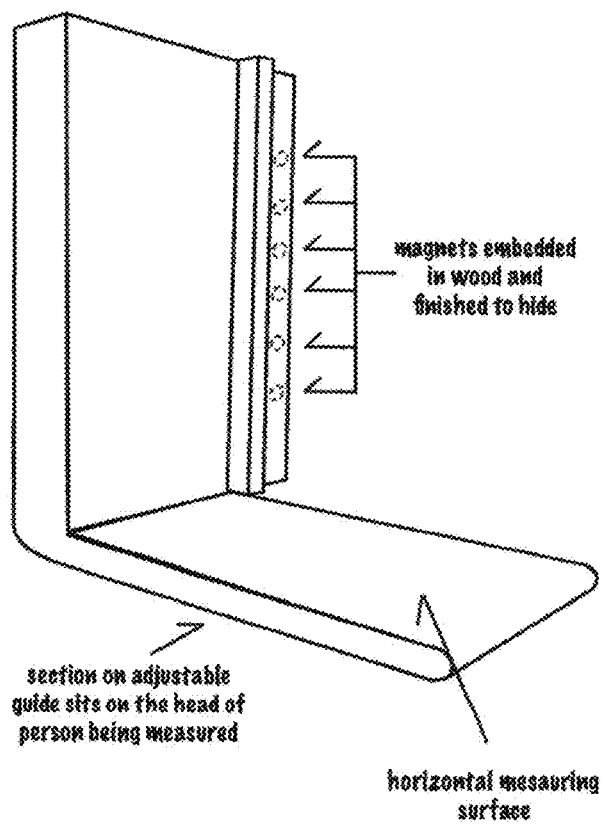
FIG. 7 depicts the height indicating guide.

FIG. 7 Height Indicating Guide Depicts the height indicating guide and identifies the location of where the hidden magnets are located. FIG. 7 shows the height indicating guide inverted to better show the flange position and a preferred position where magnets can be embedded, and preferably hidden, in the height indicating guide. These magnets slidingly maintain the height indicating guide on the metal strip on the side of the body.

FIGS. 8, 9 and 10—WALL HANGING HARDWARE

FIGS. 8 and 9 are front and side views, respectively, of magnetic wall hanging hardware which can be used to readily hang the height-measuring device. The depicted wall hanging hardware is separate from the magnetic height-measuring device. The magnetic wall hanging hardware provides the ability to affix the height-measuring device to a wall without screws or nails being put through the body and allows for ease of removal if necessary. This hardware comprises magnets on a base. One side of the base comprises two-sided tape for securing the base to a wall. Once the bases are secured to a wall, the height measuring device can easily be hung on the wall utilizing the attraction of the magnets in the hanging hardware and the body.

FIG. 10 is a depiction of the aforementioned hanging hardware, i.e., a pair of steel bars that are attached to the wall by screws so that the corresponding magnets embedded into the rear surface of the body member can be used to releasably attach the body member to the wall at a selected height such that the measuring indicia on the front face of the body member indicate their distance to the floor.

The magnetic height measuring device provides a convenient way to measure and record heights of children and adults with minimal moving parts. The embedded magnets are effective for facilitating movement of the height indicating guide and the chart board relative to the body, while being safe for children by not creating a risk of pinching small fingers or a choking hazard from small parts.

The invention claimed is:

1. A device for measuring the height of an individual subject, which comprises;
   a) an elongated body member having a front surface which visually displays units of measure, each measuring unit being divided into fractions of the measuring unit which are depicted on said surface;
   b) magnetic wall hanging hardware to attach said body member to a vertical wall surface above a generally horizontal floor surface;
   c) a height indicating guide member which is releasably and slidably attached to said body member, said slidable guide member having an outwardly extending height indicating member attached thereto, said outwardly extending height indicating member having a height measuring surface which is generally horizontal and parallel to the floor surface, such that the height of said horizontal surface above the floor surface is visually indicated on the body member, and
   d) the magnetic wall hanging hardware comprising steel bars attached to the wall with screws and corresponding magnets embedded in the elongated body member for removable attachment of the elongated body member to the wall at a selected height onto the corresponding steel bars;
   whereby when said body member is attached to a wall surface with the measurement indicia depicting the distance of the number of measurement units to the floor, positioning the individual subject adjacent the body member and sliding the guide member to a position where said horizontal height measuring surface contacts the uppermost part of the head of the individual subject, the height of the individual subject is indicated on the body member.

2. A device for measuring the height of an individual subject, which includes,
   an elongated body member having a front surface which visually displays units of measure, each measuring unit being divided into fractions of the measuring unit which are depicted on the front surface;
   the body member is attachable to a vertical wall surface above a generally horizontal floor surface by any known means, including, by attaching a pair of steel bars to the wall surface, and attaching, or embedding, a plurality of rare earth magnets to the body member, including at least two magnets for each steel bar;
   a height indicating guide member is releasably and slidably attached to the body member by a metal strip being embedded and hidden from view into a side of the body member, and several magnets, being attached or embedded into a side surface of the guide member;
   the slidable guide member having an outwardly extending height indicating member attached thereto;
   the outwardly extending height indicating member has a height measuring bottom surface which is generally horizontal and parallel to the floor surface, such that the distance between the horizontal surface and the floor surface is visually indicated on the body member;
   the body member is attached to a wall surface at a vertical position which depicts the distance between the measurement units and the floor; and, the chart board is releasably attached to the body member by a plurality of magnets;

wherein the individual subject is positioned adjacent the body member and the guide member is slid to a position where the lower horizontal height measuring surface contacts the uppermost surface of the head of the individual subject, the height of the individual subject will be indicated on the body member.

3. The device for measuring the height of an individual subject according to claim 2, which further includes:

a height information chart board that is conveniently slidably inserted into a slot of the body member, the chart board having a writing surface for recording the height of an individual subject, i.e., a child as he or she is growing up.

4. The device for measuring the height of an individual subject according to claim 2, wherein, the magnets are rare earth magnets.

5. The device for measuring the height of an individual subject according to claim 2, wherein, the body member is preferably comprised of two sections attached by hinges so that it can be folded for storage or transport.

\* \* \* \* \*